United States Patent [19]

Linden

[11] Patent Number: 5,019,038
[45] Date of Patent: May 28, 1991

[54] IRRIGATION SYSTEM FOR SURGICAL PROCEDURES

[75] Inventor: Harry A. Linden, Santa Barbara, Calif.

[73] Assignee: Hall Surgical Division of Zimmer Inc., Carpinteria, Calif.

[21] Appl. No.: 426,817

[22] Filed: Oct. 25, 1989

[51] Int. Cl.$^5$ ............................................. A61M 31/00
[52] U.S. Cl. ...................................... 604/49; 604/151; 604/22; 433/87
[58] Field of Search ............................... 606/167–170, 606/180; 604/22, 50, 51, 54, 93, 151–153, 246; 433/82, 84, 85, 87, 88

[56] References Cited

U.S. PATENT DOCUMENTS

| | | | |
|---|---|---|---|
| 816,685 | 4/1906 | Sevier | 433/87 |
| 2,012,886 | 8/1935 | Lowry | 433/85 |
| 3,237,306 | 3/1966 | Staunt | 433/84 |
| 3,949,753 | 4/1976 | Dockhorn | 433/84 X |
| 4,205,676 | 6/1980 | Humphrey et al. | 604/54 |
| 4,276,023 | 6/1981 | Phillips et al. | 433/85 |
| 4,428,748 | 1/1984 | Peyman et al. | 604/22 |
| 4,634,420 | 1/1987 | Spinosa et al. | 604/22 |

OTHER PUBLICATIONS

PCT Application WO85/00523, Norton et al., 2/14/85.

*Primary Examiner*—John D. Yasko
*Assistant Examiner*—Adam J. Cermak
*Attorney, Agent, or Firm*—Stuart Krieger

[57] ABSTRACT

An irrigation system for cooling a surgical cutting tool, cutting site and/or flushing debris from the cutting site during surgery includes a first conduit connected to a source of sterile irrigation fluid and a second conduit adapted to be supported on the cutting tool to deliver irrigation fluid to the cutting site. The irrigation system further includes a lightweight disposable pump assembly for pumping the sterile irrigation fluid from the fluid source through the first and second conduits to the cutting site. The disposable pump assembly includes a pump chamber that communicates with the first and second conduits and a flexible pump member rotatable in the pump chamber. The pump assembly and conduits are in a presterile condition to permit immediate use by a physician and are discarded after the surgical operation is completed.

8 Claims, 4 Drawing Sheets

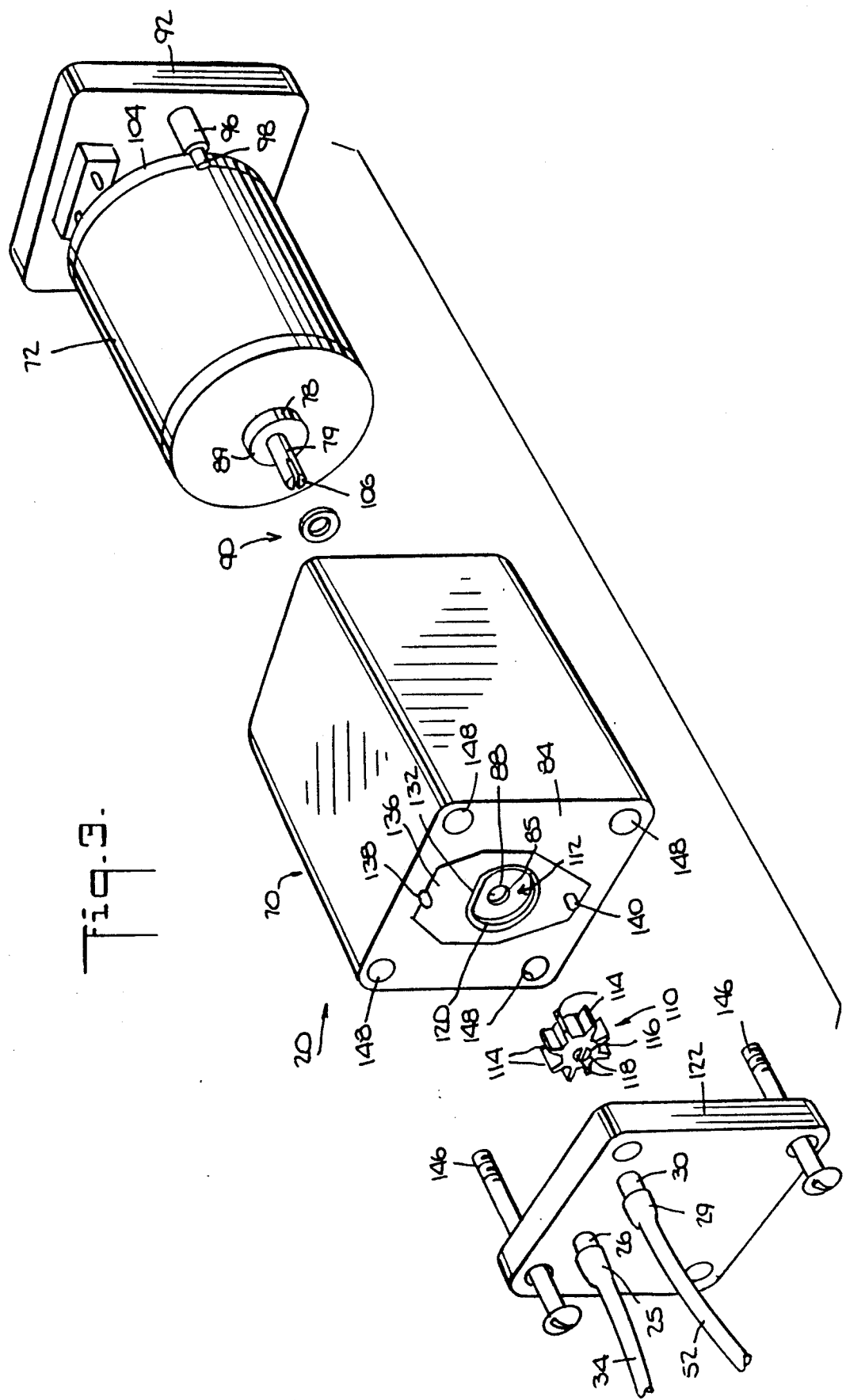

IRRIGATION SYSTEM FOR SURGICAL PROCEDURES

BACKGROUND OF THE INVENTION

This invention relates to irrigation systems for surgical procedures and, more particularly, to a lightweight, portable, disposable surgical irrigation system.

Nondisposable surgical irrigation systems that supply sterile fluid for flushing and cooling a surgical cutting site are well known. Such systems generally cool a particular region of a cutting tool or cutting site and flush the cut debris from the cutting site.

As used herein, the term "cutting" is also intended to include drilling.

Cooling the cutting tool and/or the cutting site helps keep the cut surface of bone and/or tissue at a low enough temperature to prevent thermal necrosis. A continuous removal of cut debris during the surgical cutting process usually facilitates the surgical operation and permits greater accuracy in the surgery than systems without irrigation. Surgical accuracy is particularly important in microsurgery procedures, where visual access is vital and the margin for error is extremely small.

Examples of procedures that either use or would benefit from surgical irrigation systems include oral endosseous implants, removal of third molars (wisdom teeth) when high speed drilling is required to split the tooth, otology (ear surgery) where irrigation is presently used to remove blood and debris while cutting an access hole through the temporal bone in preparation for a cochlear implant, oral maxillofacial surgery, spinal surgery, revision surgery of the femoral canal, arthroscopic surgery, orthopedic surgery, particularly total knee replacement, and other procedures.

Conventional surgical irrigation systems often employ a relatively heavy immobile reusable systolic pump with an attachable pre-sterilized tubing set. The tubing, which is disposable, is removed and discarded after a surgical procedure is completed. A typical method of attaching new tubing to the pump prior to surgery is to disassemble the pump head, insert the new tubing over the pump rollers, and reassemble the pump.

The systolic pump system evolved in response to a need for sterile irrigants. The power systems and pumps used prior to the development of the systolic system could not be effectively sterilized and therefore required an interacting sterile system. However, the systolic pump system is cumbersome to disassemble and reassemble for the purpose of replacing used tubing with sterile tubing. Furthermore, the tubing used in a systolic pump must be of a certain hardness or Durometer in order to effectively deliver a required flow of irrigant to a cutting site. Also, some training and dexterity is required to disassemble and assemble the systolic pump system.

Although the systolic system can deliver different flow rates by changing pump speed, the type of flow produced is of a pulsing nature as the systolic rollers alternately compress and release the tubing. Moreover, some low power systolic pumps require a relatively soft section of tubing, such as natural rubber, at the portion of the system that contacts the pump rollers. This need for relatively soft tubing increases the complexity of the systolic pump system and can lead to a problem of improper functioning of the pump if the tube is not correctly installed.

Another known system for delivering sterile irrigant includes a pressure vessel surrounding a flexible bag of irrigant. The bag is attached through a pressurizing device to pre-sterilized tubing. Flow of liquid through the tubing is achieved by pressurizing the container to compress the flexible bag. The tubing is removed and discarded after each surgical procedure is completed.

The pressure vessel system also has inherent problems in that a sterile interface is required between the irrigant reservoir (the flexible bag of irrigant) and the exterior tubing. A sterile interface can be accomplished with sterile fittings but is cumbersome to set up. Moreover, the pressure vessel is relatively large compared to the flexible bag of irrigant and requires a source of pressurized gas, which can explode if overpressurized or incorrectly assembled. In addition, irrigant flow must be controlled by the use of a tubing pinch roller, which is generally imprecise.

It is thus desirable to provide a completely disposable portable irrigation system that can be precisely controlled, is nonhazardous, simple to set up and use, highly mobile, and does not require any assembly or disassembly of the pumping apparatus.

OBJECTS AND SUMMARY OF THE INVENTION

Among the several objects of the invention may be noted the provision of a novel surgical irrigation system, a novel surgical irrigation system employing an inexpensive, sterilizable disposable pump assembly, a novel disposable surgical irrigation system employing a disposable pump assembly that need not be assembled or disassembled prior to use, a novel surgical irrigation system that is mobile and convenient to locate in any selected area, a novel surgical irrigation system that is easy to set up, and a novel method of irrigating a surgical cutting site with a sterile irrigation fluid.

Other objects and features of the invention will be in part apparent and in part pointed out hereinafter.

In accordance with one embodiment of the invention, the irrigation system for cooling a cutting tool and flushing debris from a cutting site during surgery includes a lightweight disposable pump with a sterile pump chamber for pumping irrigation fluid from a sterile irrigation fluid source, and a disposable sterile tubing set. The tubing set includes a first conduit connected to the source of sterile irrigation fluid and a second conduit supported on a cutting tool for delivering irrigation fluid to the cutting site. The pump chamber communicates with the first and second conduits and accommodates a sterilizable flexible rotatable pump member.

The disposable pump assembly and tubing set can thus be preassembled and packaged in a sterile condition. Under this arrangement, before a physician commences surgical cutting, all that need be done is to remove the sterile pump and sterile tubing set from the package, connect the tubing set to the source of sterile irrigation fluid, usually a flexible bag or a rigid container, and secure the delivery tube to the cutting tool. After the surgical cutting operation is completed the pump assembly and tubing set can be detached from the cutting tool and fluid source and discarded.

Preferably, the pump assembly and tubing set are preassembled prior to sterilization and are simultaneously sterilized.

The invention accordingly comprises the constructions and method hereinafter described, the scope of the invention being indicated in the claims.

BRIEF DESCRIPTION OF THE DRAWINGS

In the drawings,

FIG. 3 is an exploded perspective view of the pump assembly thereof;

Corresponding reference characters indicate corresponding parts throughout the several views of the drawings.

DETAILED DESCRIPTION OF THE INVENTION

Figure 1:
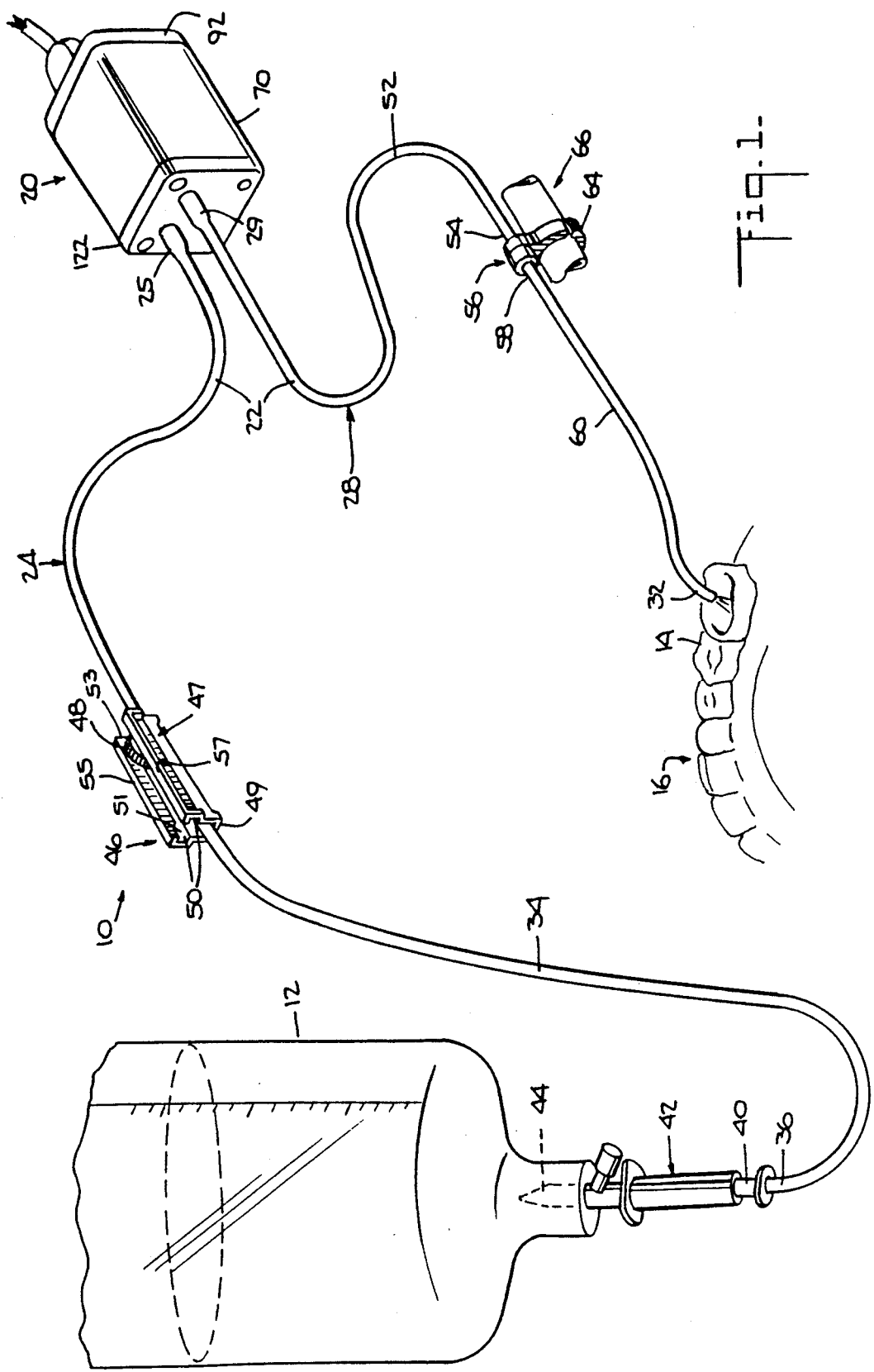
FIG. 1 is a perspective view of a surgical irrigation system incorporating one embodiment of the present invention.
Figure 2:
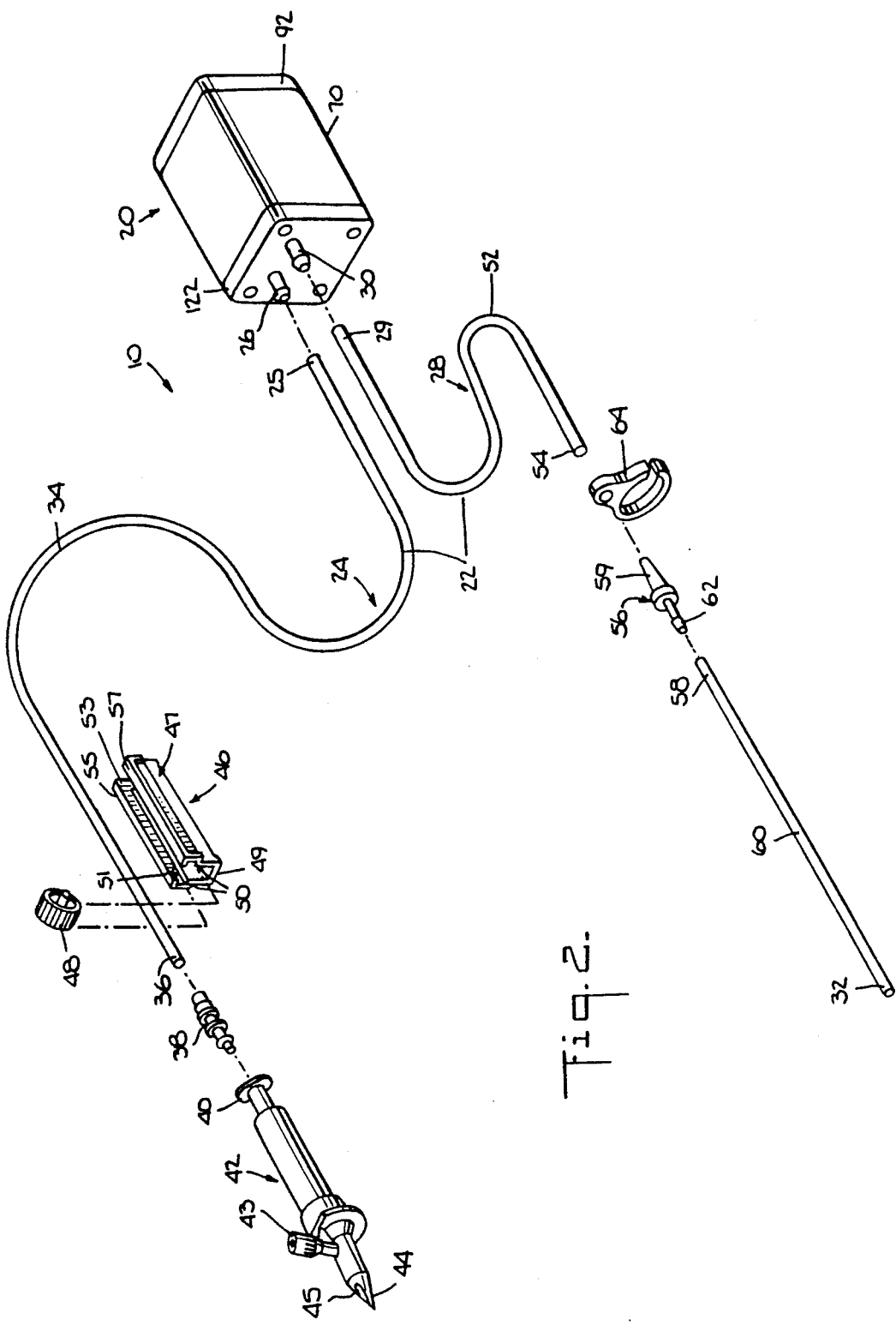
FIG. 2 is an exploded perspective view thereof.

A surgical irrigation system incorporating one embodiment of the invention is generally indicated by the reference number 10 in FIGS. 1 and 2.

The irrigation system 10 as illustrated in FIG. 1, is used for example, in connection with delivering a sterile irrigation fluid from an irrigant container 12 to a surgical cutting site such as a molar 14 in a patient's mouth, generally indicated at 16. The irrigation system 10 includes a pump assembly 20 and a tubing set 22.

The tubing set 22 includes a first conduit 24, having an end portion 25 which interconnects the irrigant container 12 with an inlet fitting 26 (FIG. 2) on the pump assembly 20. The tubing set 22 also includes a second conduit 28 having one end 29 connected to an outlet fitting 30 (FIG. 2) of the pump assembly 20. An opposite delivery end 32 of the conduit 28 delivers sterile irrigation fluid to the cutting site 14.

Referring more particularly to FIG. 2, the first conduit 24 includes a tube portion 34 that connects at one end 36 to a connector 38 which, in turn, is connected to one end 40 of a conventional stab fitting 42 having an air relief knob 43. An opposite end 44 of the stab fitting 42 is provided with a sharpened point and an opening 45 proximate the sharpened point. The pointed end 44 of the stab fitting 42 is adapted to penetrate the irrigant container 12 to permit flow of the sterile irrigation fluid from the container 12 through the surgical irrigation system 10 via the opening 45 at the sharpened point. Although not shown, a removable sterile sheath normally covers the pointed end 44 and is removed before the fitting 42 penetrates the container 12.

A flow control device 46 is mounted on the tube 34 downstream of the stab fitting 42 to control and vary the flow of irrigant fluid through the tube 34, and to completely shut off the flow when desired. The control device 46 includes a channel member 47 and a roller 48 which bears against the tube 34, which is supported along a base portion 49 of the channel 47. The roller 48 is longitudinally movable along an angled track 50 formed in side walls 55 and 57 of the channel 47 between a maximum flow position at an end 51 of the track 50 and a no flow position at an end 53 of the track 50.

Referring particularly to FIG. 2, the second conduit 28 includes a first tube portion 52 having an end 54 opposite the end 29 connected to a tapered end 59 of a fitting 56. An opposite end 62 of the fitting 56 is connected to an end 58 of a second tube 60. The opposite delivery end 32 of the tube 60 delivers irrigation fluid 32 to the cutting site 14 (FIG. 1).

A tool holder 64 is carried by the conduit 28 between the end 54 of tube 52 and the fitting 56. The tool holder 64 is adapted to detachably hold a cutting tool, schematically indicated at 66 in FIG. 1. The clamp 64 is sized to snugly embrace the cutting tool 66 and locate the tube 60 adjacent a selected part of the cutting tool.

The tube 60 is preferably formed of a suitable material that is pliable and is of a reduced diameter relative to the tube 52. For example, the tube 60 can be formed of a plastic or stainless steel tubing that can be bent to shape. The tubes 52 and 34, which can be formed of vinyl, are preferably resilient and flexible to allow freedom of movement of the cutting tool 66 and to allow freedom of movement of the irrigant container 12. The tube 60 can be a surgical grade Tygon ® tubing distributed under Part No. 0006-006 by Ryan-Herco Co. and the tubes 52 and 34 can be a surgical grade Tygon ® tubing distributed under Part No. 0006-033 by Ryan-Herco Co.

Figure 5:
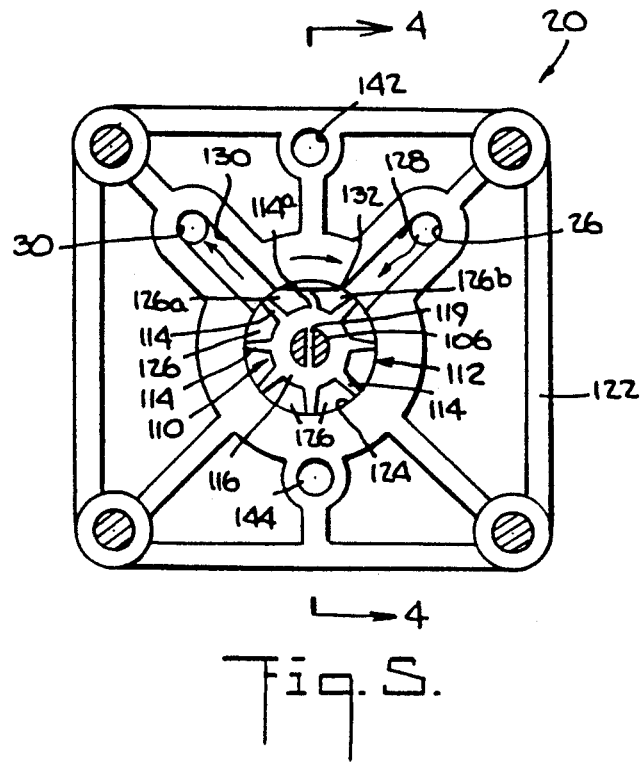
Figure 4:
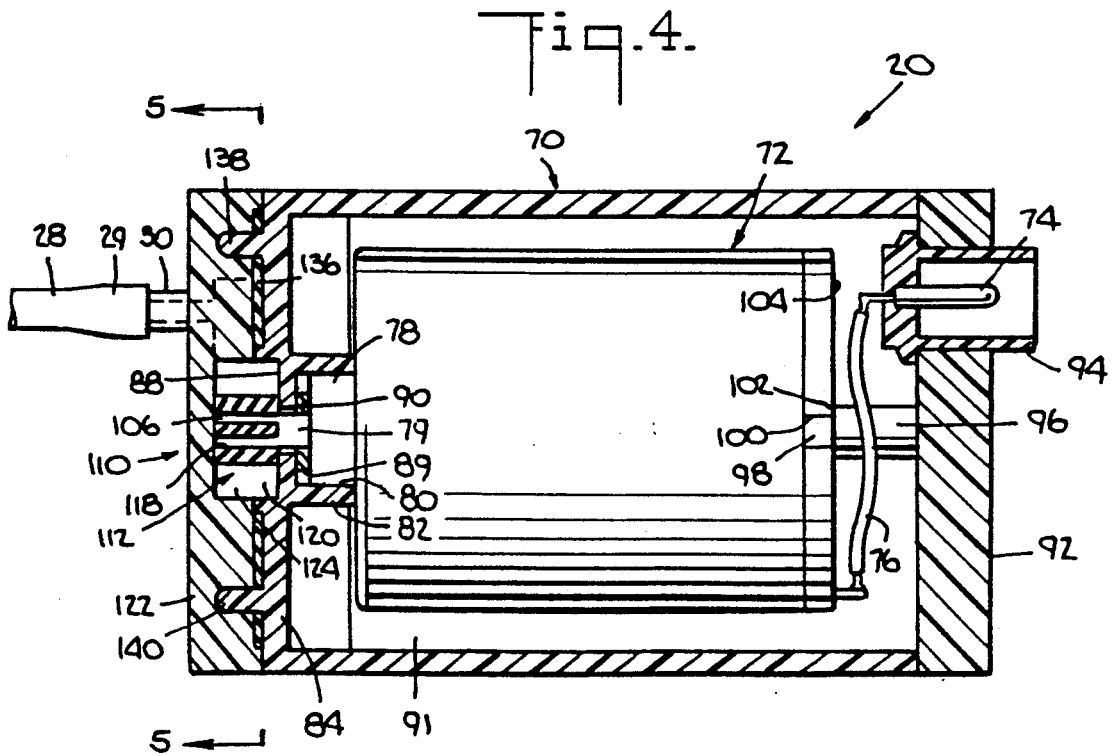
FIG. 4 is a side elevation view of the pump assembly in section, taken along the line 4—4 of FIG. 5; and, FIG. 5 is a front sectional view of the pump, taken along the line 5—5 of FIG. 4.

Referring now to FIGS. 3-5, the pump assembly 20 is a compact pump and motor unit such as a Model No. P-50 pump made by the Parker Hannifin Company. The pump assembly 20 is a lightweight unit weighing less than 6.5 ounces and has overall dimensions of approximately 1⅜ inches by 1⅜ inches by 2⅜ inches.

The pump assembly 20 comprises a housing 70 within which a low voltage variable speed DC electric drive motor 72 is supported. The housing 70 is preferably formed of rigid plastic material, such as a polyester resin. The voltage supplied to the motor 72 can be varied by a potentiometer (not shown) and is supplied to the motor via a pair of terminals, one of which is shown at 74, and a pair of wires interconnecting the terminals to the motor, one such wire being shown at 76 (FIG. 4).

Referring to FIGS. 3 and 4, a cylindrical bushing 78 is fixed to one end of the motor 72 surrounding a motor shaft 79. The cylindrical outer periphery of the bushing 78 constitutes a shoulder that is received in a recess 80 (FIG. 4) formed in an annular extension 82 that is integral with an end wall 84 of the housing 70. The bearing 78 rotatably supports the motor shaft 79, which shaft extends through a central aperture 85 (FIG. 3) formed in an offset portion 88 of the wall 84. An annular elastomeric seal 90 is disposed in the recess 80, between the offset wall portion 88 and an end surface 89 of the bearing 78, to provide a leak tight seal along the shaft 79 and thus prevent leakage of irrigation fluid into a motor chamber portion 91 of the housing 70.

A cover member 92 closes a rear end of the housing 70 and is fastened in place by any suitable known bolts (not shown). The terminals 74 are accommodated in a connector 94 which is secured in place in the cover member 92 by any suitable known adhesive.

Referring to FIG. 3, the cover member 92 includes a pair of integrally formed posts 96 that extend into the interior of the housing 70. The posts 96 are provided with reduced diameter end portions 98 that engage respective slots 100 formed at the periphery of an end wall 104 of the motor 72. Under this arrangement, the motor is prevented from rotating within the housing 70 by the posts 96. In addition, a shoulder 102 (FIG. 4) formed by a step in the posts 96 abuts against the end wall 104 of the motor 72. The shoulder 102 forces the end surface 89 of the bushing 78 into contact with the elastomeric seal 90 when the cover member 92 is locked in place, thereby enhancing the sealing effect of the seal 90.

Referring to FIGS. 3 and 4, the motor shaft 79 includes a slotted end portion 106 that projects beyond the offset portion 88 of the wall 84. The slotted end portion 106 engages a pump member 110 that is rotatable within a pump chamber 112.

The pump member 110, which is preferably formed of a resilient elastomeric material such as EPDM rubber, includes a central hub portion 116 and a plurality of flexible vanes 114 radially extending from the hub 116. The central hub portion 116 is formed with spaced semicylindrical openings 118 separated by a median portion 119 (FIG. 5). The semi-cylindrical openings 118 are adapted to receive the slotted end portion 106 of the motor shaft 79. Thus rotation of the motor shaft 79 causes rotation of the pump member 110.

The pump chamber 112 (FIGS. 3 and 4) is partially formed as a recess 120 in the end wall 84 of the housing 70, as shown in FIG. 3 and partially as a recess 124 within a pump cover member 122, as shown in FIG. 4.

As most clearly shown in FIG. 5, the pump chamber 112 is generally cylindrical in shape, having a diameter that is substantially the same as the diameter of the vaned portions 114 of the pump member 110. The pump chamber 112 is also provided with a flattened peripheral chord portion 132 which extends across an upper portion of the pump chamber 112. The axial length of the pump chamber 112 is substantially the same as the axial length of the pump member 110. Thus the vanes 114, the end walls 84, 122 and peripheral walls 120, 124 of the pump chamber form subchambers 126 that rotate about the chamber 112 along with the vanes 114.

Referring to FIG. 5, irrigation fluid that enters the pump assembly 20 via the inlet 26 is led into the pump chamber 112 by an internal inlet passageway 128 formed in the pump cover member 122. Similarly, irrigation fluid is led from the pump chamber 112 to the outlet 30 of the pump assembly 20 via an internal outlet passageway 130 formed in the pump cover member 122.

A pumping action between the inlet passageway 128 and the outlet passageway 130 is developed when the vanes 114 which rotate across the flattened portion 132 deflect and assume the position shown by vane 114a in FIG. 5. Deflection of the vanes 114 reduces the volume of the subchamber 126a that communicates with the outlet passageway 130, and increases the volume of the subchamber 126b that communicates with the inlet passageway 128. In this manner, irrigation fluid is pumped out of the subchamber 126a and through the passageway 130 to the outlet 30, and irrigation fluid is introduced from the inlet 26 through the passageway 128 into the subchamber 126b, thereby effecting a pumping action in the pump assembly 20.

A suitable elastomeric gasket 136 (FIGS. 3 and 4) is disposed between the end wall 84 of the housing 70 and the pump cover member 122 to prevent leakage of irrigation fluid between the two members during operation of the pump assembly 20.

The end wall 84 of the housing 70 is formed with a pair of pins 138 and 140 to engage corresponding apertures 142 and 144 in the pump cover member 122. The pins 138 and 140 help align the pump cover member 122 relative to the housing 70, thereby ensuring that the pump chamber portions 124 and 120 of the pump chamber 112 are in proper alignment when the pump cover member 122 is fastened to the shell 70.

Corner fasteners 146, which engage with threaded apertures 148, fasten the cover member 122 to the shell 70 such that the gasket 136 forms a leak tight seal therebetween. The pump assembly 20 is thus compact and made of relatively inexpensive materials and components. The pump assembly 20 and the tubing sets 22 can be simultaneously sterilized by, for example, conventional radiation sterilization, and packaged in a sterile condition to permit convenient and immediate use.

In using the system 10, a suitable power supply (not shown) is connected through the connector 94 and the terminals 74 (FIG. 4) to control the operating speed of the motor 72 and thus the flow rate of irrigation fluid delivered to the cutting site. Such control may be accomplished with a conventional potentiometer actuated by a control knob or foot pedal (not shown).

The surgical irrigation system 10 is thus used to irrigate a surgical cutting site 14 during surgical cutting by provision of a disposable pump assembly 20 and a disposable tubing set 22 that are connected to one another and to a source of sterile irrigation fluid 12 to deliver the irrigation fluid to the surgical cutting site. The pump assembly 20 and the tubing set 22 are sterilized prior to commencing the surgical cutting, and the surgical cutting site 14 is irrigated during the surgical cutting. After the surgical cutting operation is completed, the pump assembly and tubing set can be discarded.

Preferably, the pump assembly and tubing set are connected together and sterilized simultaneously. In this manner nothing further need be done to the pump and the tubing set by a physician before connection to the source of sterile irrigation fluid. The pump can also be of a configuration other than a vane pump, such as a gear, diaphragm or impulse pump.

Some advantages of the present invention evident from the foregoing description include a surgical irrigation system that requires no assembly or disassembly of a pump head or a pressure vessel. The surgical irrigation system is easily and economically sterilized and convenient to use, is portable, lightweight and relatively inexpensive. The pump and tubing assembly can be simultaneously sterilized and packaged in a sterile condition ready for immediate use by a physician.

In the context of the costs involved in surgery and the disadvantages inherent in the use of the prior art systolic and pressure vessel systems for surgical irrigation, the surgical irrigation system of the present invention can be manufactured and packaged at a low enough cost to permit the irrigation system to be discarded after each surgical session. Set up problems, contamination problems and immobility problems of known irrigation systems are thus dealt with and solved.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A method of irrigating a surgical cutting site during a surgical cutting operation comprising connecting a lightweight disposable pump assembly to a disposable tubing set, sterilizing the pump assembly and tubing set, packaging said sterile pump assembly and sterile tubing set in a container which maintains the sterile conditions, opening said container and removing said sterile disposable lightweight pump assembly and disposable tubing set, connecting the pump assembly and tubing set to a source of sterile irrigation fluid to deliver fluid to said surgical cutting site, irrigating the surgical cutting site during said surgical cutting, and discarding the pump assembly and the tubing set after completion of the surgical cutting operation.

2. The method as claimed in claim 1, wherein said pump assembly and the tubing set are connected together prior to sterilization and are simultaneously sterilized during said sterilization step, said method including the further step of connecting said tubing set to the source of sterile irrigation fluid after said pump assembly and said tubing set have been sterilized.

3. A method of irrigating a surgical cutting site with a sterile irrigation fluid comprising connecting a disposable tubing set to a lightweight pump assembly and pumping fluid through the tubing set with a resilient multivane pump member by flexing the vanes during rotation of the pump member to create a pumping action between an inlet and an outlet of the pump chamber, interconnecting a source of sterile irrigation fluid to said inlet to pump fluid from the inlet to the outlet and to the surgical cutting site, and simultaneously irradiating the pump assembly and the inlet and outlet tubing connected thereto to sterilize the pump assembly and inlet and outlet tubing prior to connecting the inlet tubing to the source of sterile irrigation fluid.

4. The method as claimed in claim 3, further including discarding the tubing and pump assembly after completion of the surgical cutting operation.

5. A method of irrigating a surgical cutting site with a sterile irrigation fluid during a surgical operation which comprises the steps of
providing a kit having components which include a lightweight disposable pump assembly and disposable inlet and outlet tubing,
sterilizing said kit components,
packaging said kit components in a container which maintains said kit components in a sterile condition,
opening said container,
providing a sterile irrigation fluid source,
operably connecting said kit components with the sterile irrigation fluid source,
pumping the sterile irrigating fluid through said operably connected kit components to the surgical cutting site, and
disposing of the kit components.

6. The method of claim 5 wherein said sterilizing step includes simultaneously sterilizing the kit components by irradiation.

7. The method of claim 5 wherein said providing step includes assembling the kit components so that the inlet and outlet tubing are operably connected to the lightweight disposable pump assembly.

8. The method of claim 5 wherein said sterilizing step occurs while the kit components are in a container.

* * * * *